United States Patent
Ford et al.

(10) Patent No.: US 12,089,935 B2
(45) Date of Patent: Sep. 17, 2024

(54) HYPODERMIC NEEDLE THAT MITIGATES BLOOD VESSEL COLLAPSE

(71) Applicants: K. B. Ford, Orlando, FL (US); Ronald C. Hankins, Orlando, FL (US); Michael B. Morgan, Odessa, FL (US)

(72) Inventors: K. B. Ford, Orlando, FL (US); Ronald C. Hankins, Orlando, FL (US); Michael B. Morgan, Odessa, FL (US)

( * ) Notice: Subject to any disclaimer, the term of this patent is extended or adjusted under 35 U.S.C. 154(b) by 0 days.

(21) Appl. No.: 17/847,427

(22) Filed: Jun. 23, 2022

(65) Prior Publication Data

US 2023/0075969 A1 Mar. 9, 2023

Related U.S. Application Data

(60) Provisional application No. 63/240,452, filed on Sep. 3, 2021.

(51) Int. Cl.
*A61B 5/15* (2006.01)
*A61M 29/00* (2006.01)

(52) U.S. Cl.
CPC ....... *A61B 5/150396* (2013.01); *A61M 29/00* (2013.01)

(58) Field of Classification Search
CPC .... A61B 5/15–15003; A61B 5/150206; A61B 5/150374–150396; A61B 5/150412; A61B 5/150427; A61B 8/445; A61B 5/15007; A61B 5/150435; A61B 8/4455; A61B 5/150244; A61B 5/150251; A61B 5/150267; A61B 5/150282; A61B 5/15029; A61B 5/150297; A61B 5/150305; A61B 5/150503; A61B 5/150511; A61B 5/150526; A61B 5/150534; A61M 29/00–02

See application file for complete search history.

(56) References Cited

U.S. PATENT DOCUMENTS

| | | |
|---|---|---|
| 4,995,866 A | 2/1991 | Amplatz et al. |
| 5,292,310 A | 3/1994 | Yoon |
| 5,330,432 A | 7/1994 | Yoon |
| 6,436,119 B1 | 8/2002 | Erb et al. |
| 7,189,217 B2 | 3/2007 | Chang et al. |
| 2004/0049223 A1 | 3/2004 | Nishtala et al. |

(Continued)

FOREIGN PATENT DOCUMENTS

| | | | | |
|---|---|---|---|---|
| EP | 1602328 A1 | * | 12/2005 | ........... A61B 5/1422 |
| WO | WO-2006029370 A2 | * | 3/2006 | ......... A61B 17/3478 |

(Continued)

OTHER PUBLICATIONS

International Search Report of Sep. 28, 2022 for PCT/US22/34649.
U.S. Appl. No. 63/240,452, filed Sep. 3, 2021; "Catheter Needle System".

*Primary Examiner* — Yi-Shan Yang
*Assistant Examiner* — Om Patel
(74) *Attorney, Agent, or Firm* — Christopher M. Ramsey; GrayRobinson, P.A.

(57) ABSTRACT

An apparatus includes a hypodermic needle, a blood vessel dilator connected to the hypodermic needle, and an actuator connected to the blood vessel dilator in such a way that the actuator expands the blood vessel dilator. The blood vessel dilator helps mitigate blood vessel collapse.

16 Claims, 9 Drawing Sheets

(56) References Cited

U.S. PATENT DOCUMENTS

| | | | |
|---|---|---|---|
| 2005/0010178 A1* | 1/2005 | Katz | A61B 5/150396 604/272 |
| 2006/0287574 A1* | 12/2006 | Chin | A61M 29/02 606/198 |
| 2014/0058429 A1* | 2/2014 | Tegels | A61B 17/0057 606/191 |
| 2014/0074141 A1* | 3/2014 | Johnson | A61M 25/10182 606/192 |
| 2015/0246211 A1 | 9/2015 | Bunch et al. | |
| 2018/0028314 A1* | 2/2018 | Ekvall | A61M 25/0102 |
| 2019/0247627 A1* | 8/2019 | Korkuch | A61M 25/0097 |
| 2020/0094025 A1* | 3/2020 | Wisman | A61M 29/00 |
| 2020/0367924 A1* | 11/2020 | Lenker | A61B 17/320783 |

FOREIGN PATENT DOCUMENTS

| | | | | |
|---|---|---|---|---|
| WO | WO-2007046850 A2 * | 4/2007 | | A61M 25/0606 |
| WO | WO-2018055450 A2 * | 3/2018 | | A61B 1/00082 |
| WO | WO-2020191228 A1 * | 9/2020 | | A61M 25/0097 |

\* cited by examiner

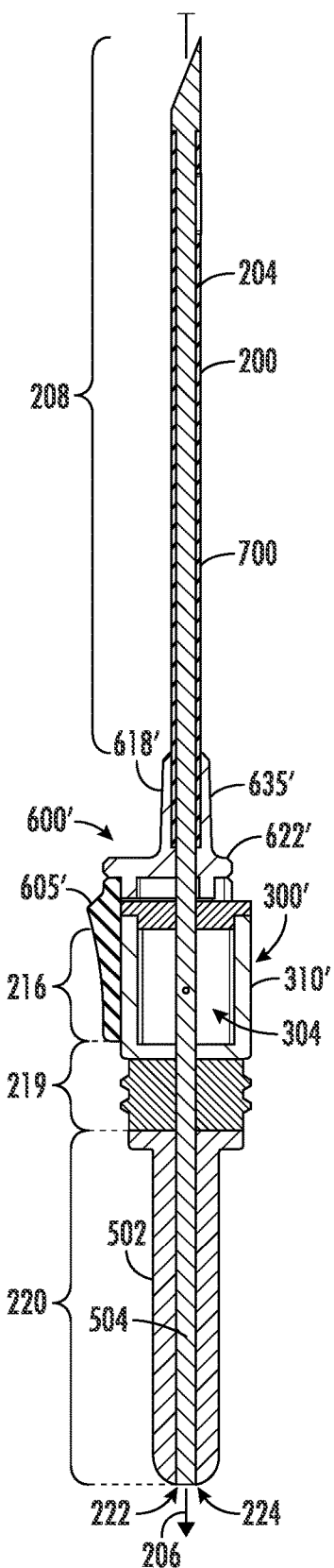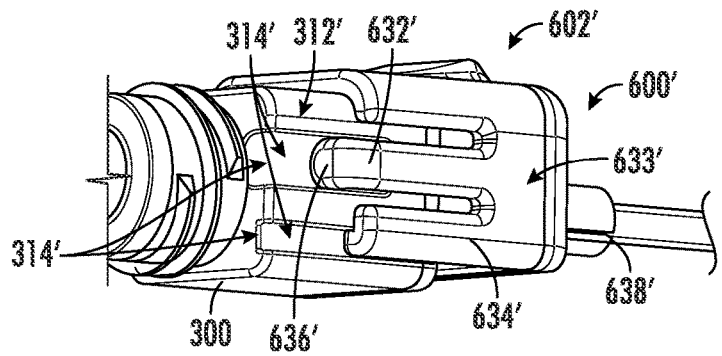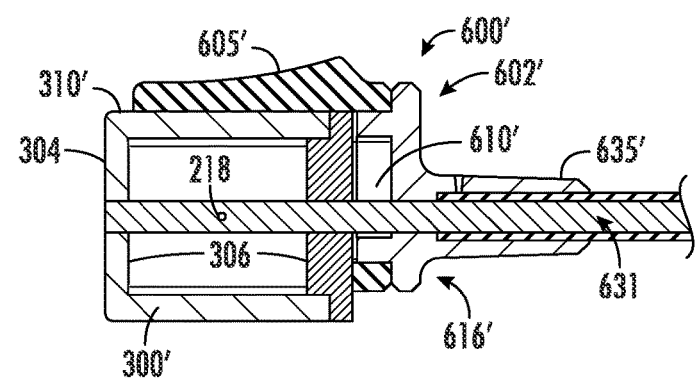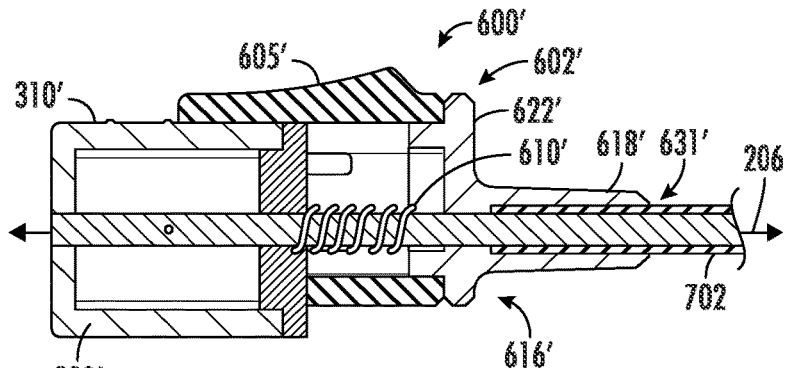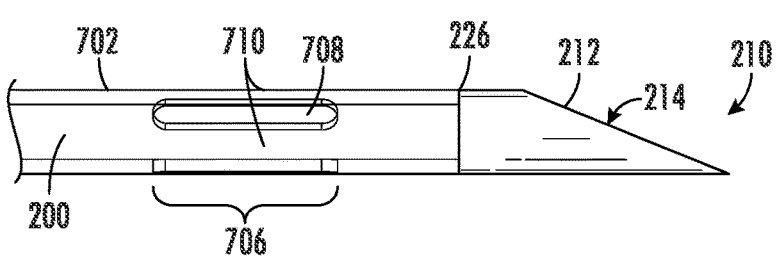

HYPODERMIC NEEDLE THAT MITIGATES BLOOD VESSEL COLLAPSE

CROSS-REFERENCE TO RELATED APPLICATION

This claims the benefit of priority to U.S. provisional Application No. 63/240,452, filed Sep. 3, 2021, which is incorporated by reference in its entirety.

FIELD

This relates to the field of medical devices and, more particularly, to hypodermic needles.

BACKGROUND

When medical professionals draw blood from patients, they often have difficulty inserting the needle into the patient's blood vessel and extracting blood. One reason for this is that some patients have collapsing veins. Another reason is that the vacuum tubes used to withdraw and collect blood from patients can suck the vessel closed. Multiple needle insertions, which are painful, are often required. This is particularly problematic if a patient has to have blood drawn on a frequent basis.

BRIEF SUMMARY

An example of an apparatus that overcomes these drawbacks includes a hypodermic needle, a blood vessel dilator connected to the hypodermic needle, and an actuator connected to the blood vessel dilator in such a way that the actuator expands the blood vessel dilator. The apparatus may further include one or more of the following features.

The actuator may be connected to the blood vessel dilator through a sheath over the hypodermic needle.

The blood vessel dilator may include a sheath over the hypodermic needle, the sheath having an expandable section proximal to a pointed terminal end of the hypodermic needle.

The hypodermic needle may include an axis extending through a lumen thereof and the blood vessel dilator may expand around the axis.

The hypodermic needle may include an axis extending through a lumen thereof. The blood vessel dilator may include a sheath over the hypodermic needle. The sheath may have an expandable section. Compressing the sheath along the axis may cause the expandable section to expand.

The hypodermic needle may include a pointed terminal end and a sheath stop adjacent the pointed terminal end. The blood vessel dilator may include a sheath having a proximal end moveable by the actuator and a distal end contacting the sheath stop.

The actuator may automatically contract the blood vessel dilator when the actuator is disengaged.

Another example of an apparatus that overcomes these drawbacks includes a hypodermic needle including an axis extending through a lumen thereof and a compressible blood vessel dilator over the hypodermic needle. The blood vessel dilator has an expandable section. An actuator is connected to the blood vessel dilator in such a way that the actuator compresses the blood vessel dilator thereby causing the expandable section to expand. The apparatus may further include one or more of the following features.

The blood vessel dilator may include a compressible sheath over the hypodermic needle and the actuator may compress the sheath.

The blood vessel dilator may include a sheath over the hypodermic needle. The sheath may include the expandable section. The expandable section may be located proximal to a pointed terminal end of the hypodermic needle.

The expandable section may expand around the axis.

The hypodermic needle may include a pointed terminal end and a sheath stop adjacent the pointed terminal end. The blood vessel dilator may include a sheath including the expandable section. The sheath may have a proximal end moveable by the actuator and a distal end contacting the sheath stop. The actuator may be connected to the blood vessel dilator by contacting the sheath.

An example of a method of mitigating blood vessel collapse while extracting blood from a blood vessel having a hypodermic needle therein includes engaging an actuator that causes a blood vessel dilator over the hypodermic needle to expand about the hypodermic needle toward a wall of the blood vessel. The method may further include one or more of the following features.

The actuator may be engaged by applying force thereto.

The method may further include contracting the blood vessel dilator by removing force from the actuator.

The actuator may be connected to the blood vessel dilator through a sheath over the hypodermic needle.

The blood vessel dilator may include a sheath over the hypodermic needle, the sheath having an expandable section proximal to a pointed terminal end of the hypodermic needle.

The hypodermic needle may include an axis extending through a lumen thereof and the blood vessel dilator may expand around the axis.

The hypodermic needle may include an axis extending through a lumen thereof. The blood vessel dilator may include a sheath over the hypodermic needle, the sheath having an expandable section. Compressing the sheath along the axis may cause the expandable section to expand.

The hypodermic needle includes a pointed terminal end and a sheath stop adjacent the pointed terminal end. The blood vessel dilator may include a sheath having a proximal end moveable by the actuator and a distal end contacting the sheath stop.

These examples of the apparatus and method may include any combination of the aforementioned features.

BRIEF DESCRIPTION OF THE DRAWINGS

FIG. 14 is a side sectional view thereof.

FIG. 15 is a close up perspective view thereof showing the flash chamber and actuator.

FIG. 16 is a close up sectional view thereof showing the flash chamber and actuator when the actuator is in its disengaged position.

FIG. 17 is a close up sectional view thereof showing the flash chamber and actuator when the actuator is in its engaged position.

FIG. 18 is a close up view thereof of a portion of the hypodermic needle insertion section.

DETAILED DESCRIPTION OF EXAMPLE EMBODIMENTS

Figure 1:
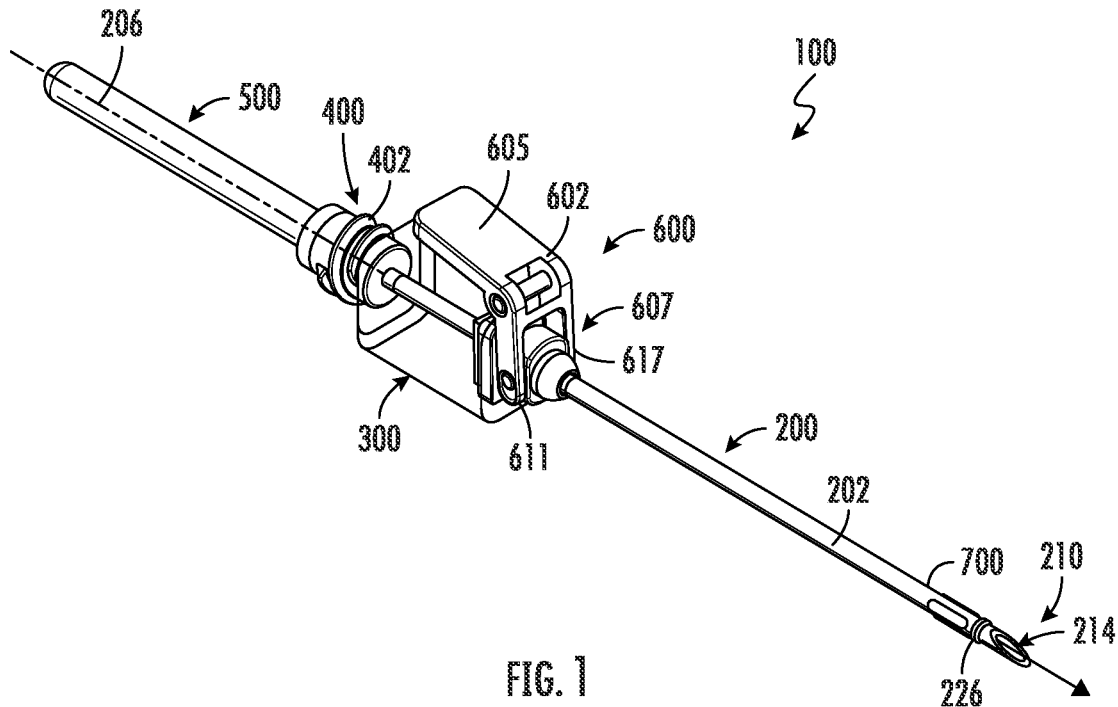
FIG. 1 is a top perspective view of a first example of the apparatus.
Figure 2:
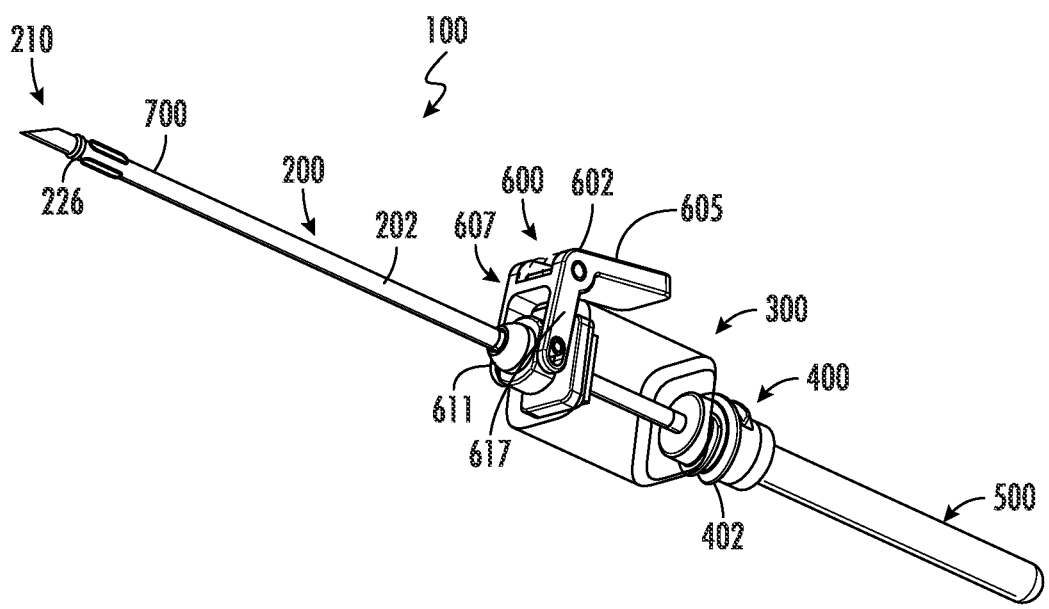
FIG. 2 is a bottom perspective view thereof.
Figure 3:
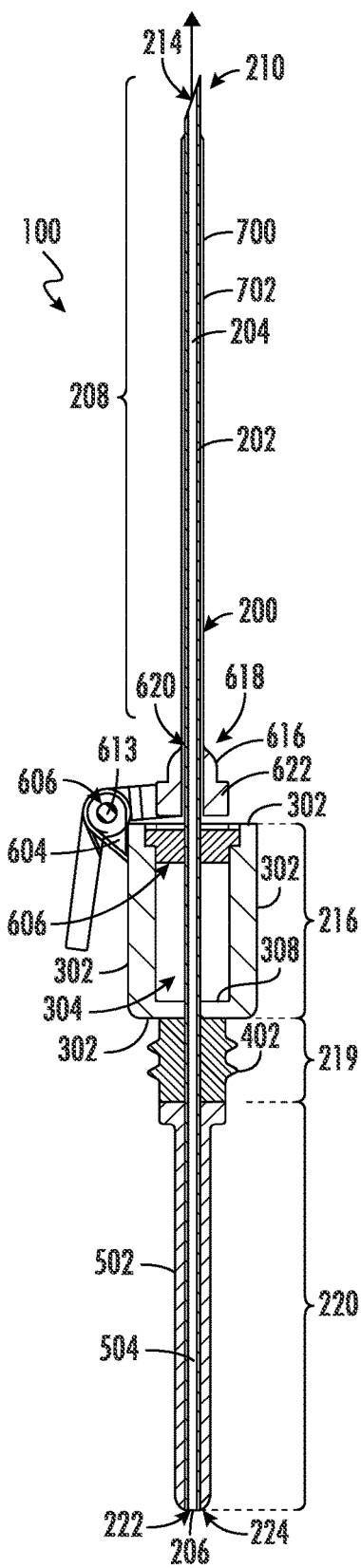
FIG. 3 is a side sectional view thereof.

This disclosure describes features and examples, but not all possible features and examples of the apparatus. Where a particular feature is disclosed in the context of a particular example, that feature can also be used, to the extent possible, in combination with and/or in the context of other features and examples. The apparatus and related methods may be embodied in many different forms and should not be construed as limited to only the features and examples described here.

Referring to FIGS. 1-11, a first example of the apparatus 100 includes a hypodermic needle 200, a flash chamber 300, a hub 400, a sleeve 500, an actuator 600, and a blood vessel dilator 700.

The hypodermic needle 200 is designed to be partially inserted under the skin of a human or animal patient and into a blood vessel for withdrawing a blood sample from the patient's blood vessel. The hypodermic needle 200 may be made of conventional material from which conventional hypodermic needles are made and may have the dimensions of conventional hypodermic needles. Common gauges for blood draw and venipuncture needles are 18-23 gauge needles.

The hypodermic needle 200 includes a shaft 202 defining a lumen 204 passing through a central axis 206 of the shaft 202. The shaft 202 includes an insertion section 208 designed to be inserted into the patient. The insertion section 208 includes a pointed end 210 with a bevel 212 defining a first needle opening 214 providing access to the lumen 204.

Figure 5:
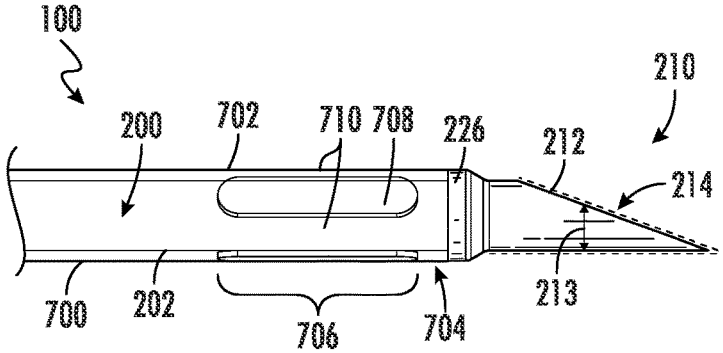
FIG. 5 is a close up view thereof showing a portion of the hypodermic needle insertion section.

As shown in FIG. 5, the bevel 212 defines a bevel angle 213 between the surface of the bevel 212 and the bottom surface of the hypodermic needle 200 to the point. The bevel angle 213 may be any angle used on conventional hypodermic needles. In certain examples, however, it may be advantageous make the bevel angle 213 from 10 degrees to 20 degrees, 10 degrees to 15 degrees, 15 degrees to 20 degrees, or from 12 degrees to 13 degrees. Having a steeper bevel angle 213 may provide less painful entry into the skin and vessel as well as reduce the tendency to skate over the surface of the vessel, thereby minimizing damage and potential vein rupture and collapse. Also, the longer more gradual aperture of the first needle opening 214 may provide less tendency for red blood cell shear stress/hemolysis.

The hypodermic needle 200 includes sheath stop 226 positioned near the pointed end 210. The sheath stop 226 is a radially enlarged section of the hypodermic needle 200 that extends around the circumference of the radially constricted section of the hypodermic needle 200. The sheath stop 226 has a circumference that is the same as or closely approximates the circumference of the sheath 702.

The hypodermic needle includes a flash chamber section 216 passing through the flash chamber 300. The flash chamber section 216 of the hypodermic needle 200 defines a flash opening 218 through the shaft 202 and providing access to the lumen 204.

The hypodermic needle includes a hub section 219 passing through the hub 400 and a sleeve section 220 passing through the sleeve 500. The lumen 204 continues from the first needle opening 214 to the sleeve section end 222. The sleeve section end 222 defines a second needle opening 224 through which blood extracted from the patient can exit into a blood collection container such as a vacuum tube or the like.

The flash chamber 300 may provide a visible indication to medical personnel that blood is flowing through the lumen 204. The flash chamber includes a plurality of flash chamber sidewalls 302 defining a hollow space 304 extending from a flash chamber first end 306 to a flash chamber second end 308. The flash chamber section 216 of the hypodermic needle 200 extends through the flash chamber 300 and the flash opening 218 is positioned within the hollow space 304. At least a portion of the flash chamber sidewalls 302 may be transparent. In use, when blood flows through the lumen 204, a portion of the blood will exit the flash opening 218 into the flash chamber 300, which informs medical personnel that blood is in the lumen 204.

The hub 400 is designed to be attached to a blood container holder that receives the blood container into which drawn blood is stored. The hub 400 includes a fastener 402 for attachment to a cooperating portion of the holder that mates with the fastener 402. In the examples shown, the fastener 402 takes the form of screw threads, but there are many other fastener types that may be used because the fastener 402 merely has to be fastened to the holder.

The sleeve 500 includes a sleeve sidewall 502 defining a sleeve space 504 in which the sleeve section 220 of the hypodermic needle 200 is located. The sleeve may be made of resilient material such as a rubber or rubber-like material. When the apparatus 100 is not being used, the sleeve 500 covers the sleeve section 220 of the hypodermic needle 200. When the apparatus is in use, the sleeve section 220 of the hypodermic needle 200 is inserted into the blood container and the sleeve sidewall 502 collapses. When the blood container is removed, the sleeve sidewall 502 expands to cover the sleeve section 220 of the hypodermic needle 200 once again.

The actuator 600 is connected to the blood vessel dilator 700 in such a way that the actuator 600 expands the blood vessel dilator 700. This objective can be achieved in many ways by mechanically connecting the actuator 600 to the blood vessel dilator 700.

In the example of FIGS. 1-11, the actuator 600 is connected to the flash chamber 300 at a connection point 603 on the flash chamber 300. The connection point 603 includes a pair of opposed stanchions 604, each stanchion 604 defining an axle receiving hole 606 passing therethrough. The axle receiving holes 606 receive an axle 613 connected to a moveable member 602.

The moveable member 602 is designed to rotate about the axle 613 when pressed downwardly by a human finger. A biasing member 610 about the axle 613 is biased against the moveable member 602 holding the moveable member 602 in a naturally disengaged position in which the blood vessel dilator 700 is not expanded. A rotational axis 612 passing through the axle 613 defines the rotational axis of the moveable member 602.

The moveable member 602 includes a finger contact member 605 positioned on top of the flash chamber 300 and extending rearwardly away from the pointed end 210 of the hypodermic needle 200. The finger contact member 605 defines a pair of opposed fulcrum openings 615 that receive the axle 613. The finger contact member 605 includes a lateral width perpendicular to the central axis 206 and a longitudinal length along the central axis 206 suitable for approximating the size of a human finger pad.

The moveable member 602 includes an extension member 607 extending downwardly from the fulcrum openings 615 forward the flash chamber 300 toward the central axis 206. The extension member 607 includes a first arm 611 and a second arm 617 on opposed sides of the central axis 206. The first arm 611 and second arm 617 define a respective nub opening 614. A blood vessel dilator receiving member 616 is at least partially positioned in the space between the first arm 611 and second arm 617.

The blood vessel dilator receiving member 616 includes a forward protuberance 618 surrounding the hypodermic needle 200. The forward protuberance 618 extends radially around the hypodermic needle 200 and defines a needle passage 620 through which the hypodermic needle 200 extends.

The forward protuberance 618 protrudes from a base 622 that extends radially around the hypodermic needle 200. The needle passage 620 continues through the base to a rearward base end 624. The base includes opposed nubs 626 positioned on opposite sides thereof along a nub axis 628 that is substantially perpendicular to and bisects the central axis 206. The nubs fit into the respective nub openings 614 to connect the blood vessel dilator receiving member 616 to the moveable member 602. The nub openings 614 are vertically elongated to permit the nubs 626 to move therein when the actuator 600 is engaged and disengaged.

The blood vessel dilator receiving member 616 is connected to the blood vessel dilator 700 in such a way that, when the blood vessel dilator receiving member 616 moves in response to engagement or disengagement of the moveable member 602, the blood vessel dilator 700 expands and contracts.

In the examples shown in the drawings, the blood vessel dilator 700 includes a sheath 702 made of thin-walled, tubular, flexible, plastic or plastic-like material that extends over the insertion section 208 of the hypodermic needle 200 from the blood vessel dilator receiving member 616 to a distal end 704 that is near the pointed end 210. The distal end 704 abuts the sheath stop 226.

The sheath 702 may be made of any surgically acceptable plastic or plastic-like material such as silicone, polyurethane, polyethylene, polypropylene, or the like.

The sheath 702 includes an expandable section 706 that can expand and retract in response to movement of the actuator 600. The expandable section 706 may be placed anywhere along the sheath 702. The expandable section 706 is typically, but not always, closer to the pointed end 210 than the blood vessel dilator receiving member 616. In the examples shown, the expandable section 706 is positioned near the pointed end 210 in order to hold the blood vessel open near the lumen 204 while blood is being drawn from the patient.

The expandable section 706 may be constructed in different ways. In the examples shown, the expandable section 706 is constructed of valleys 708 and peaks 710 that radially alternate about the central axis 206. By positioning valleys 708 between the peaks 710, this allows the peaks 710 to bend radially outward relative to the central axis 206 when the sheath is compressed along the central axis 206.

In some examples, the valleys 708 may be thinned sections of sheath 702 compared to the wall thickness of the remaining portions of the sheath 702. In other examples, as shown in FIGS. 1-11, the valleys 708 may be slits passing through the wall thickness of the sheath 702. The peaks 710, on the other hand, are continuous from the adjacent sections of the sheath 702. The peaks 710 may have the same wall thickness as the rest of the sheath 702 apart from the valleys 708 or may have increased wall thickness relative to the rest of the sheath 702.

Figure 4:
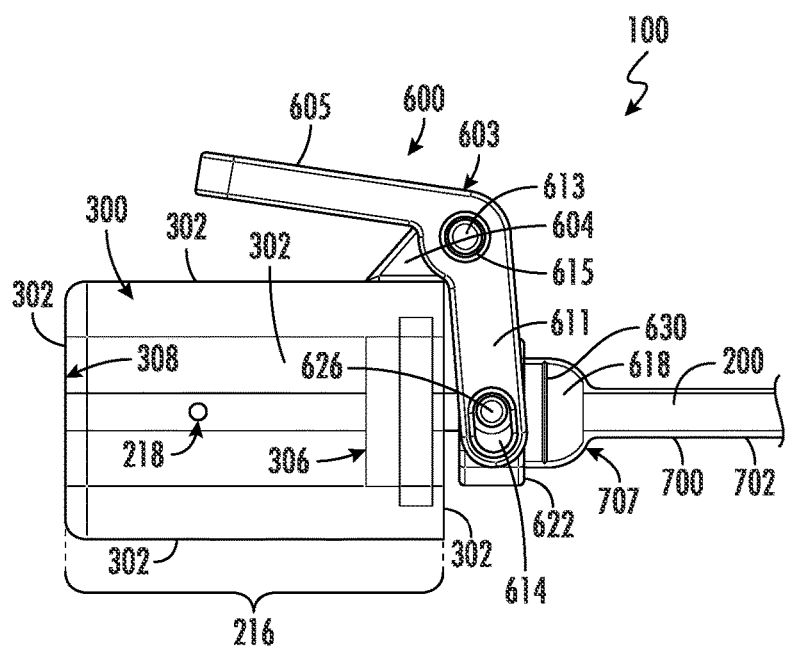
FIG. 4 is a close up view of the flash chamber and actuator thereof.

As best seen in FIG. 4, the blood vessel dilator receiving member 616 is connected to the sheath 702 at a radially enlarged end 707 of the sheath 702. The radially enlarged end 707 is tightly stretched over the protuberance 618 to abut the base 622. A raised ridge 630 extending radially out of the protuberance 618 around the circumference of the protuberance 618 presses against the inside diameter of the sheath 702 to help secure the sheath to the protuberance 618.

Figure 6:
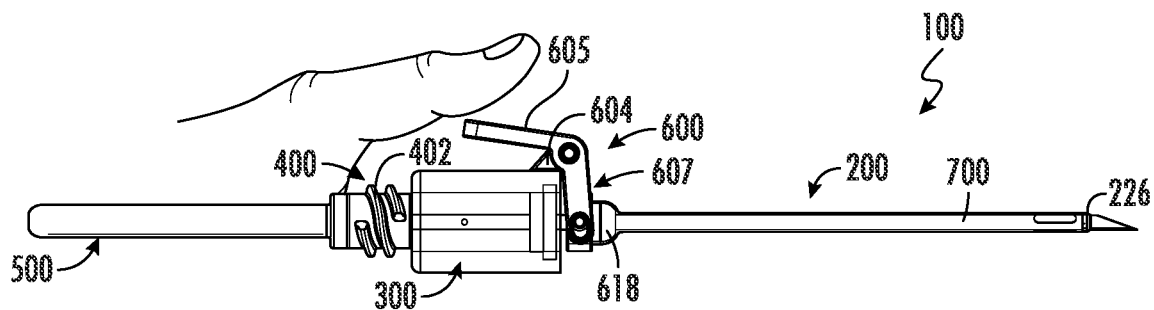
FIG. 6 is a side view thereof with the actuator in its disengaged position.
Figure 7:
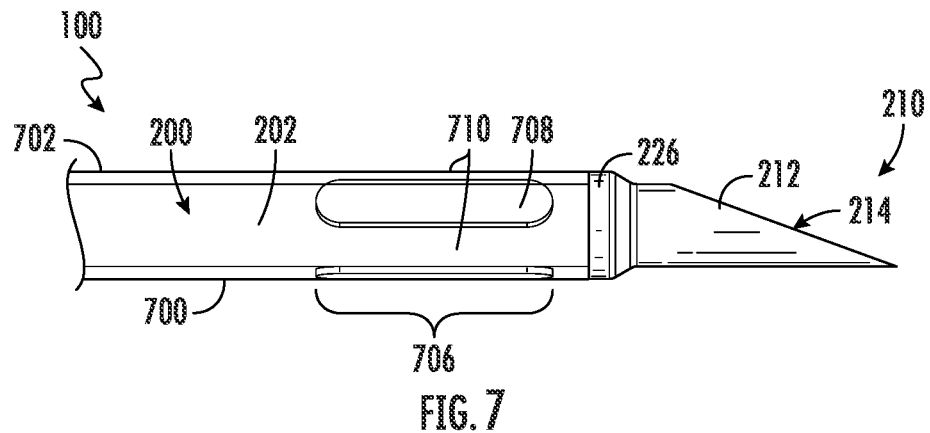
FIG. 7 is a close up view thereof showing a portion of the hypodermic needle insertion section when the actuator is in its disengaged position.
Figure 8:
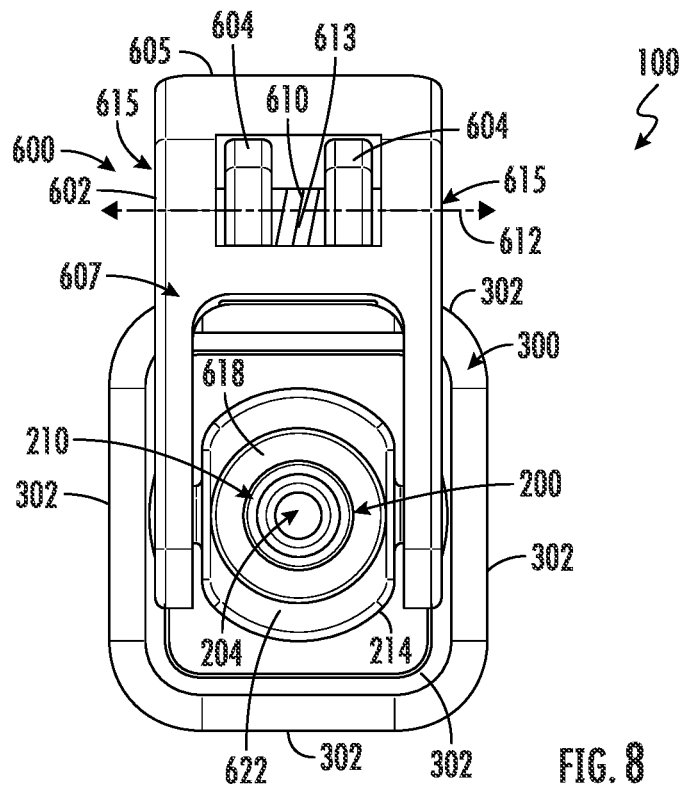
FIG. 8 is a front view thereof when the actuator is in its disengaged position.

Referring now to FIGS. 6-8, the actuator 600 is shown in a disengaged position in which the finger contact member 605 is not being pressed by a human finger. In the disengaged position, the biasing member 610 biases the finger contact member 605 upwardly and the extension member 607 rearwardly toward the flash chamber 300. This position keeps the sheath 702 extended along the hypodermic needle 200, which maintains the expandable section 706 in a collapsed state.

Figure 9:
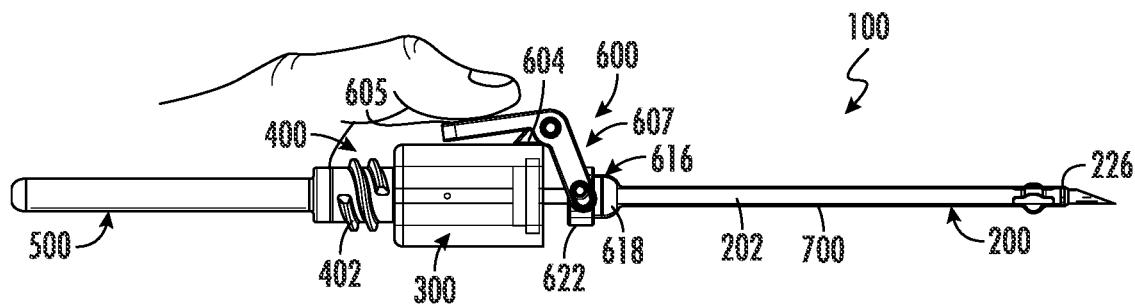
FIG. 9 is a side view thereof with the actuator in its engaged position.
Figure 10:
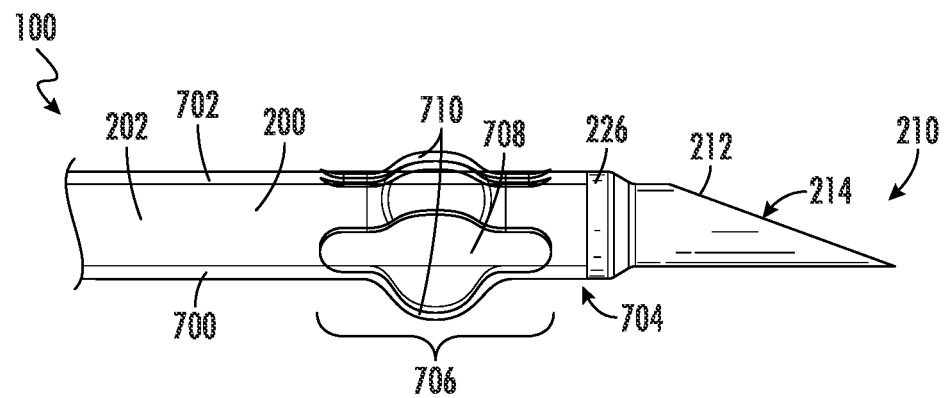
FIG. 10 is a close up view thereof of a portion of the hypodermic needle insertion section when the actuator is in its engaged position.
Figure 11:
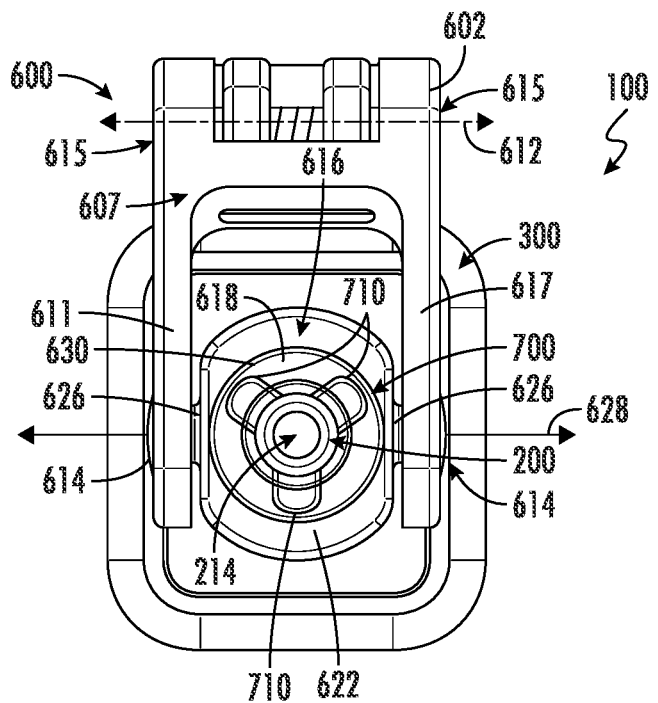
FIG. 11 is a front view thereof when the actuator is in its engaged position.
Figure 12:
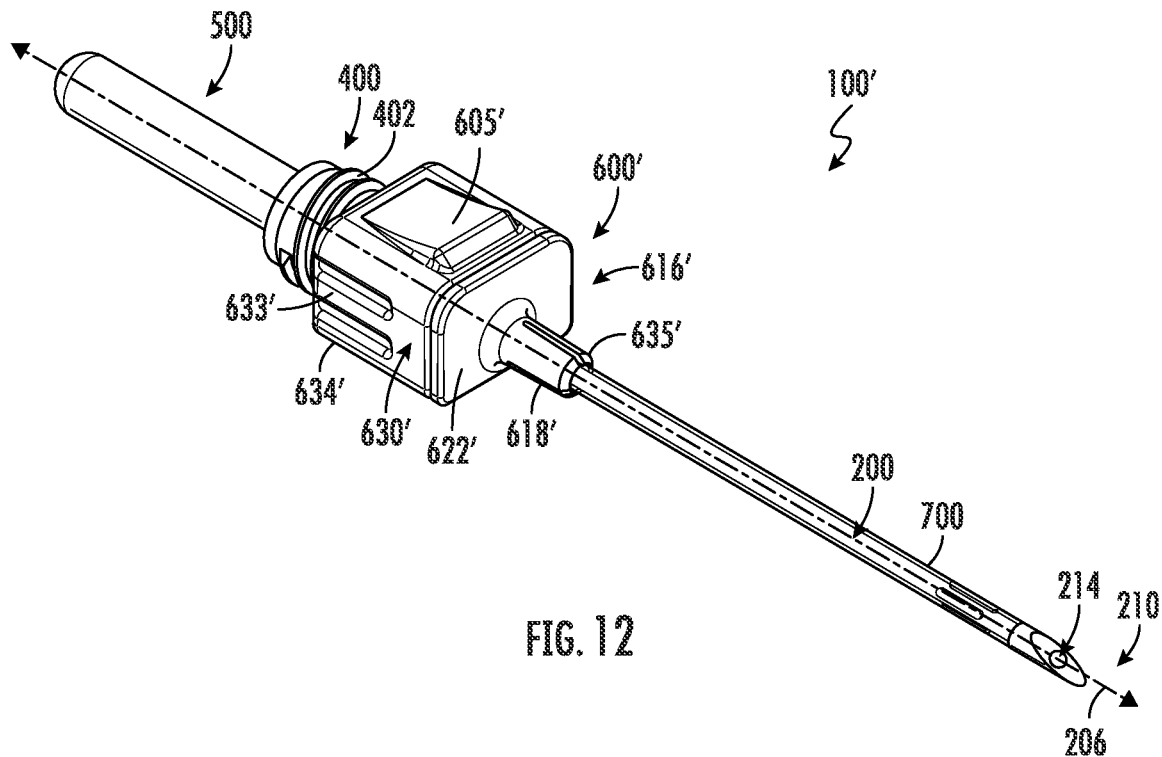
FIG. 12 is a top perspective view of a second example of the apparatus.
Figure 13:
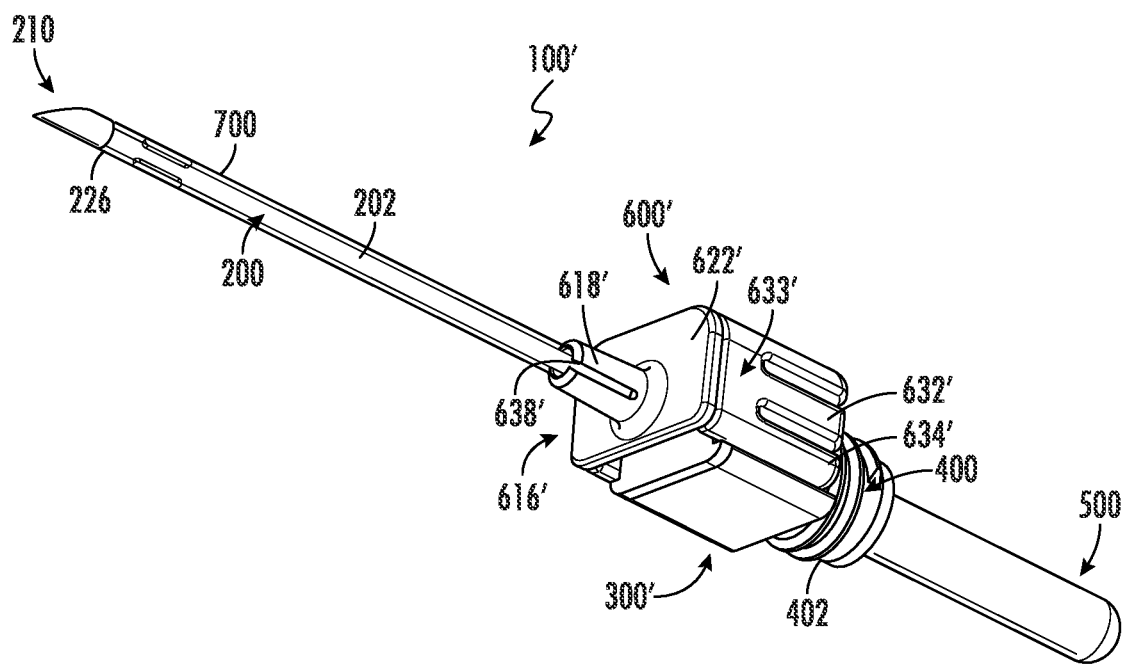
FIG. 13 is a bottom perspective view thereof.

In comparison, FIGS. 9-11 show the actuator 600 in an engaged position in which the finger contact member 605 is being pressed downwardly by a human finger. In the engaged position, the blood vessel dilator receiving member 616 moves down the hypodermic needle 200 towards the pointed end 210. This movement compresses the sheath 702 against the sheath stop 226. Compressing the sheath 702 causes the expandable section 706 to expand radially around the hypodermic needle 200. When expanded, the peaks 710 bend about their respective centers and move radially outward away from the central axis 206.

A second example of the apparatus 100' will now be described by referring to FIGS. 12-24. The second example of the apparatus 100' is substantially the same as the first example of the apparatus 100, except for how the flash chamber 300 and actuator 600 are constructed. Because of these similarities, the above description of the first example of the apparatus 100 also describes the second example of the apparatus 100'. Accordingly, to avoid being redundant, only the features of the apparatus 100' that differ from apparatus 100 are discussed below. The same reference numerals are used to represent the corresponding features in apparatus 100'. Reference numerals with a prime "'" symbol are used to represent different features in the second example of the apparatus 100'.

Relative to apparatus 100, apparatus 100' includes a different example of the flash chamber 300' and actuator 600'.

The flash chamber 300' includes an exterior surface 310' having sides 312' with a plurality of grooves 314' formed therein and running parallel to the central axis 206.

As best seen in FIGS. 15-17, the actuator 600' includes a moveable member 602' that is biased rearwardly away from the pointed end 210 when in the disengaged position using a biasing member 610'. In this example, the biasing member 610' is a spring or the like that can extend and retract along the central axis 206. The biasing member 610' is naturally in the retracted position and will expand when the finger contact member 605' is pushed forward toward the pointed end 210 into the engaged position. Expanding the biasing member 610' creates a spring force tending to pull the moveable member 602' rearwardly when user removes the user's finger from the finger contact member 605'.

The moveable member 602' includes opposed lateral sides 633', including a plurality of upper fingers 632' and lower fingers 634' that cooperatively mate with the grooves 314'. The upper fingers 632' and lower fingers 634' slide along the grooves 314' when the moveable member 602' is moved between the disengaged and engaged positions. The upper fingers 632' include an end section 636' that is turned inwardly toward the central axis 206 to form a hook like shape. This end section 636' prevents the upper fingers 632' from sliding out of the grooves 314'.

The blood vessel dilator receiving member 616' includes a base 622' on a forward end of the moveable member 602' and a protuberance 618' extending forward out of the base 622'. The protuberance 618' includes a tubular wall 635' extending radially around the hypodermic needle 200 with a tubular wall hole 631' about the central axis 206 through which the hypodermic needle 200 passes. The tubular wall 630' includes a plurality of splits 638' extend from the tubular wall hole 631' rearwardly toward the base 622'. The splits 638' are separated radially around the central axis 206.

As best seen in FIG. 17, the blood vessel dilator receiving member 616' is connected to the sheath 702 at the protuberance 618'. The sheath 702 is tightly fit into the tubular wall hole 631'. The inside diameter wall 634 presses inwardly toward the central axis 206 against the sheath 702 to help secure the sheath to the actuator 600'.

Figure 19:
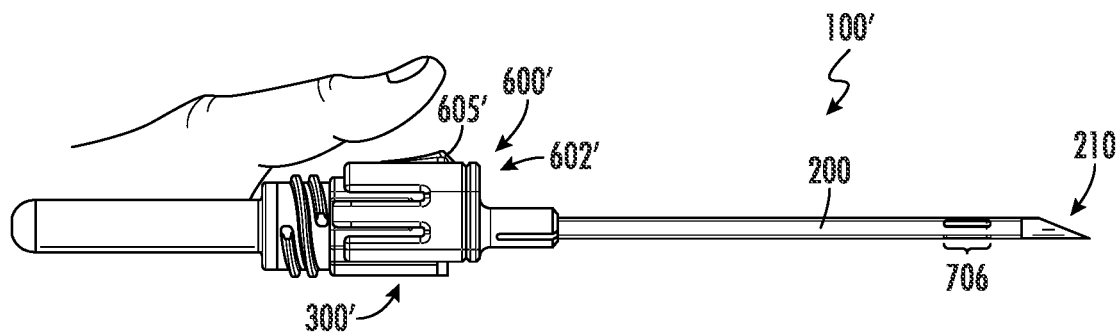
FIG. 19 is a side view thereof with the actuator in its disengaged position.
Figure 20:
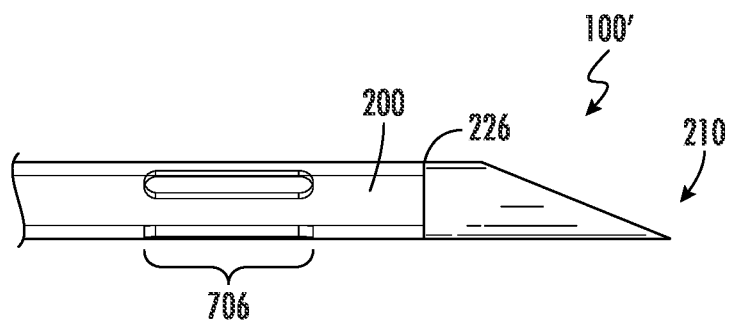
FIG. 20 is a close up view thereof showing a portion of the hypodermic needle insertion section when the actuator is in its disengaged position.
Figure 21:
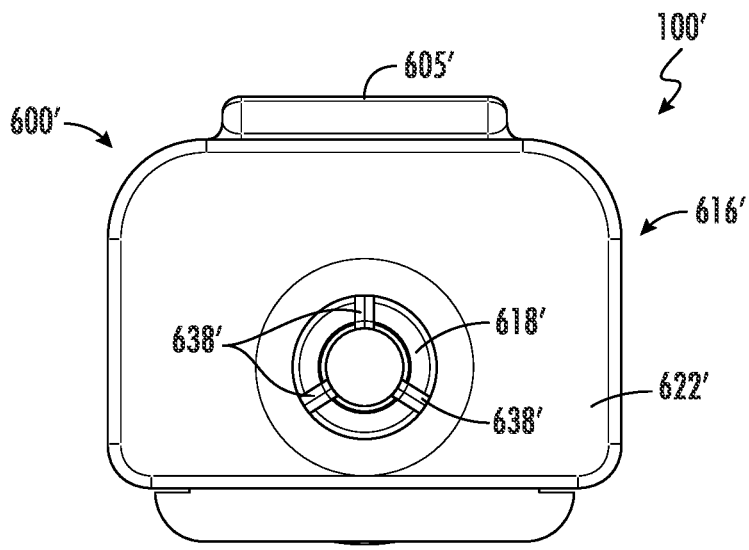
FIG. 21 is a front view thereof when the actuator is in its disengaged position.

Referring now to FIGS. 19-21, the actuator 600' is shown in the disengaged position in which the finger contact member 605' is not being pressed by a human finger. In the disengaged position, the biasing member 610' biases the moveable member 602' rearwardly towards the flash chamber 300'. This position keeps the sheath 702 extended along the hypodermic needle 200, which maintains the expandable section 706 in a collapsed state.

Figure 22:
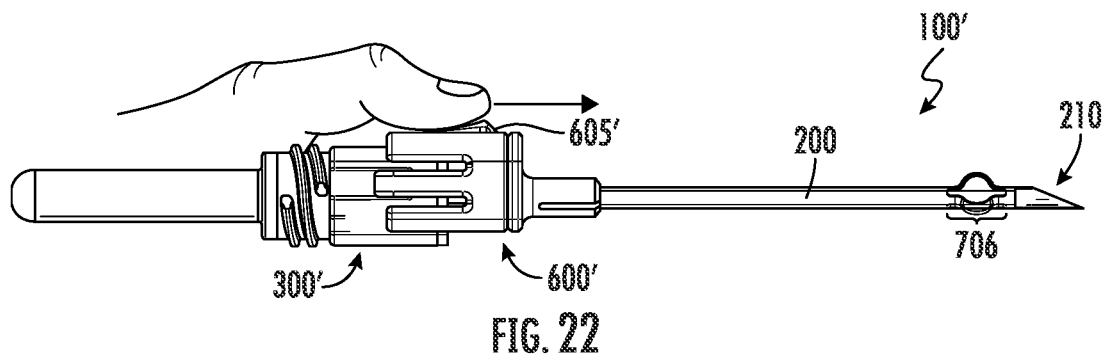
FIG. 22 is a side view thereof with the actuator in its engaged position.
Figure 23:
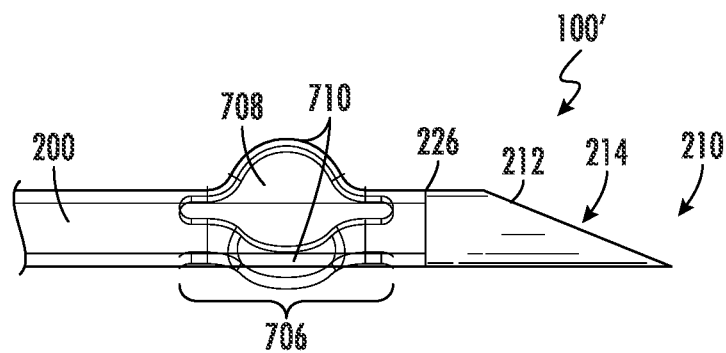
FIG. 23 is a close up view thereof of a portion of the hypodermic needle insertion section when the actuator is in its engaged position.
Figure 24:
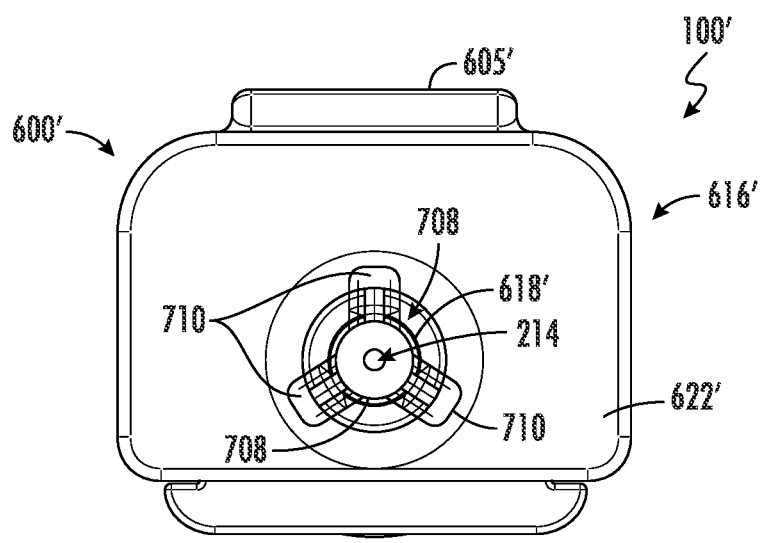
FIG. 24 is a front view thereof when the actuator is in its engaged position.

In comparison, FIGS. 22-24 show the actuator 600' in the engaged position in which the finger contact member 605' is being pressed forward by a human finger. In the engaged position, the blood vessel dilator receiving member 616' moves down the hypodermic needle 200 towards the pointed end 210. This movement compresses the sheath 702 against the sheath stop 226. Compressing the sheath 702 causes the expandable section 706 to expand radially around the hypodermic needle 200. When expanded, the peaks 710 bend about their respective centers and move radially outward away from the central axis 206.

Figure 25:
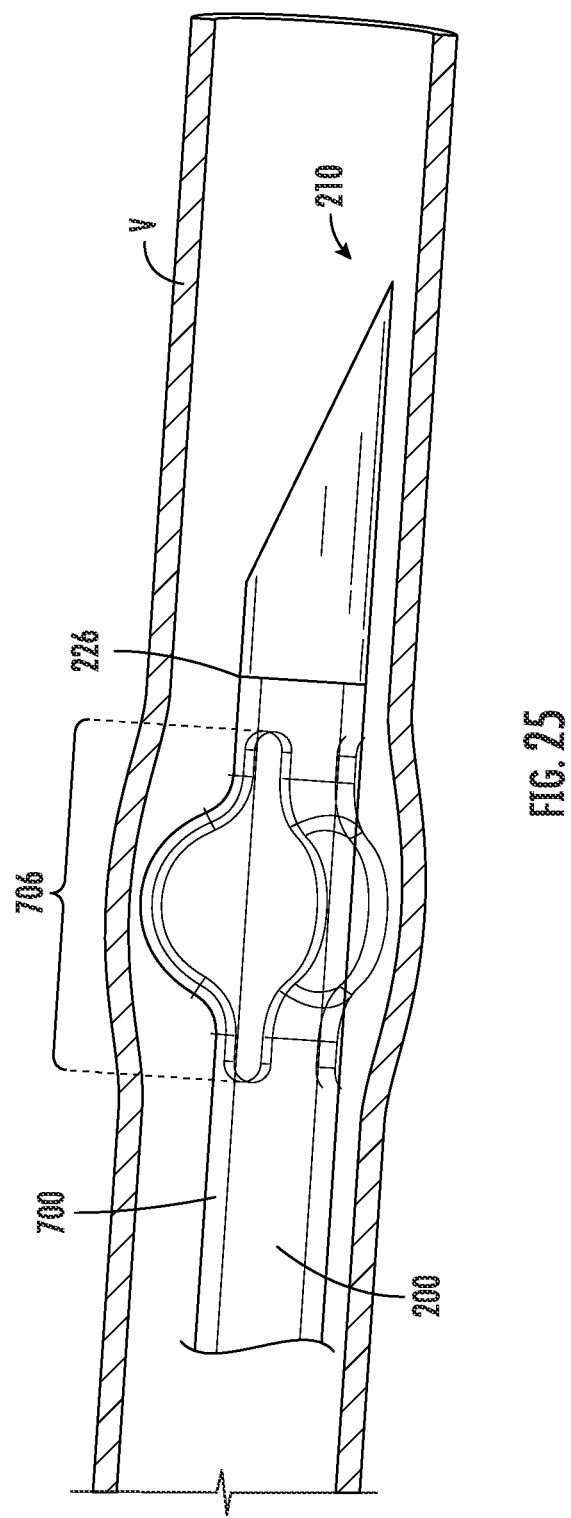
FIG. 25 is a cutaway view of a blood vessel having the hypodermic needle therein when the actuator is in the engaged position.

Referring now to FIG. 25, a portion of the hypodermic needle 200 is shown inserted into a blood vessel V to further illustrate how the expandable section 706 is advantageous. When a blood draw is performed, a user will insert at least a portion of the insertion section 208 of the hypodermic needle 200 into a patient's blood vessel with the actuator in the disengaged position. If a vacuum tube is used to contain the blood drawn from the patient, the vacuum may cause the blood vessel to collapse. The user can mitigate blood vessel collapse by moving the actuator 600, 600' into the engaged position, which causes the expandable section 706 to expand within the vessel V toward the inner wall of the vessel V and hold the vessel V open during the procedure. When the user desires to stop drawing blood, the user can remove the force the user is applying to the finger contact member 605, 605' to keep the actuator in the engaged position, which automatically, due to the biasing member's 610, 610' opposing force, will disengage the actuator 600, 600' thereby causing the expandable section 706 to collapse. Once the actuator 600, 600' is disengaged, the user may remove the hypodermic needle 200 from the patient's skin.

Although the apparatus 100, 100' is described above in connection with extracting blood from a patient, this is but one of many possible advantageous uses of the apparatus 100, 100'. The apparatus 100, 100' may be used in any situation in which it is useful to mitigate collapse of a tubular structure around a hypodermic needle.

This document refers to particular features of the apparatus and related methods. Although certain features may be described in combination with a particular example, it is to be understood that a feature described with respect to one example may be used in any of the other examples to the extent possible.

The apparatus and methods may be modified in many different ways without departing from the scope of what is claimed. The scope of the claims is not limited to only the particular features and examples described above.

That which is claimed is:

1. An apparatus comprising:
   a hypodermic needle;
   a blood vessel dilator connected to the hypodermic needle; and
   an actuator connected to the blood vessel dilator in such a way that the actuator expands the blood vessel dilator;
   wherein:
   the hypodermic needle includes a pointed terminal end and a sheath stop adjacent the pointed terminal end;
   the blood vessel dilator includes a sheath having a proximal end moveable by the actuator and a distal end contacting the sheath stop;
   the hypodermic needle includes an axis extending through a lumen thereof; and
   the sheath is over the hypodermic needle, the sheath having an expandable section that is expandable by compressing the sheath along the axis with the actuator.

2. The apparatus of claim 1, wherein the actuator is connected to the blood vessel dilator through the sheath.

3. The apparatus of claim 1, wherein the expandable section is proximal to the pointed terminal end of the hypodermic needle.

4. The apparatus of claim 1, wherein the blood vessel dilator is expandable around the axis.

5. The apparatus of claim 1, wherein the actuator has an engaged position in which the actuator expands the blood vessel dilator when a user applies force to the actuator and a disengaged position in which the actuator contracts the blood vessel dilator when the user does not apply the force to the actuator and the actuator automatically moves from the engaged position to the disengaged position when the user removes the force from the actuator.

6. The apparatus of claim 1, wherein:
the sheath stop is a radially enlarged section of the hypodermic needle; and
the proximal end is in mechanical contact with the actuator in such a way that actuating the actuator moves the proximal end which causes the sheath to expand.

7. An apparatus comprising:
a hypodermic needle including an axis extending through a lumen thereof;
a compressible blood vessel dilator over the hypodermic needle, the blood vessel dilator having an expandable section;
a flash chamber positioned about the axis around the hypodermic needle, the flash chamber housing a flash opening of the hypodermic needle for providing a visible indication of blood flow through the lumen;
an actuator on the flash chamber, the actuator being connected to the blood vessel dilator in such a way that the actuator compresses the blood vessel dilator thereby causing the expandable section to expand, the actuator including a blood vessel dilator receiving member positioned on a first side of the flash chamber and that receives the blood vessel dilator and slides along the axis to compress the blood vessel dilator, the hypodermic needle extending through the blood vessel dilator receiving member;
a hub positioned about the axis around the hypodermic needle on a second side of the flash chamber opposite the first side; and
a sleeve positioned about the axis and extending from the hub, the sleeve including resilient material that covers an opening of the hypodermic needle through which blood extracted through the lumen exits the lumen.

8. The apparatus of claim 7, wherein:
the blood vessel dilator includes a compressible sheath over the hypodermic needle; and
the sheath is compressible by moving the actuator.

9. The apparatus of claim 7, wherein the blood vessel dilator includes a sheath over the hypodermic needle, the sheath including the expandable section, the expandable section being located proximal to a pointed terminal end of the hypodermic needle.

10. The apparatus of claim 7, wherein the expandable section is expandable around the axis.

11. The apparatus of claim 7, wherein:
the hypodermic needle includes a pointed terminal end and a sheath stop adjacent the pointed terminal end;
the blood vessel dilator includes a sheath including the expandable section, the sheath having a proximal end moveable by the actuator and a distal end contacting the sheath stop; and
the actuator is connected to the blood vessel dilator by contacting the sheath with the blood vessel dilator receiving member.

12. An apparatus comprising:
a hypodermic needle;
a blood vessel dilator connected to the hypodermic needle; and
an actuator connected to the blood vessel dilator in such a way that the actuator expands the blood vessel dilator; wherein:
the hypodermic needle includes a pointed terminal end and a sheath stop adjacent the pointed terminal end;
the blood vessel dilator includes a sheath having a proximal end moveable by the actuator and a distal end contacting the sheath stop;
the sheath stop is a radially enlarged section of the hypodermic needle; and
the proximal end is in mechanical contact with the actuator in such a way that actuating the actuator moves the proximal end which causes the sheath to expand.

13. The apparatus of claim 12, wherein the actuator is connected to the blood vessel dilator through the sheath, the sheath being over the hypodermic needle.

14. The apparatus of claim 12, wherein the sheath is over the hypodermic needle, the sheath having an expandable section proximal to the pointed terminal end.

15. The apparatus of claim 12, wherein the hypodermic needle includes an axis extending through a lumen thereof and the blood vessel dilator is expandable around the axis.

16. The apparatus of claim 12, wherein the actuator has an engaged position in which the actuator expands the blood vessel dilator when a user applies force to the actuator and a disengaged position in which the actuator contracts the blood vessel dilator when the user does not apply the force to the actuator and the actuator automatically moves from the engaged position to the disengaged position when the user removes the force from the actuator.

* * * * *